United States Patent [19]

Yamamoto

[11] 4,290,673
[45] Sep. 22, 1981

[54] SKI GOGGLES

[75] Inventor: Tamenobu Yamamoto, Higashi-Osaka, Japan

[73] Assignee: Yamamoto Bojin Megane Co., Ltd., Higashi-Osaka, Japan

[21] Appl. No.: 116,598

[22] Filed: Jan. 29, 1980

[30] Foreign Application Priority Data

May 14, 1979 [JP] Japan .................. 54-59277

[51] Int. Cl.³ .................. G02C 11/08; A61F 9/02
[52] U.S. Cl. .................. 351/62; 2/437
[58] Field of Search .................. 351/62; 2/435, 436, 2/437; 55/387, 527, 158

[56] References Cited

U.S. PATENT DOCUMENTS 2,539,284  1/1951  Thomas .................. 2/436
3,377,626  4/1966  Smith.

FOREIGN PATENT DOCUMENTS 49-76981  7/1974  Japan.

*Primary Examiner*—John K. Corbin
*Assistant Examiner*—Rodney B. Bovernick
*Attorney, Agent, or Firm*—Armstrong, Nikaido, Marmelstein & Kubovcik

[57] ABSTRACT

Ski goggles comprising a goggle frame, a rubber band and a plastics goggle lens composed of a pair of inner and outer lens plates and having a heat insulating interior space between the lens plates. The inner lens plate is formed with an air port at its one end close to the frame and provided with a water-repellent air-permeable filter opposed to the air port. The filter comprises an air-permeable backing sheet and a layer of ethylene tetrafluoride resin fibers. The filter can be housed in a filter frame with an air flow regulating valve accommodated in the filter frame. The air port may be provided, in place of the filter, with a bellows container or an elastic container serving as a pressure balancing container and disposed in the goggle frame.

6 Claims, 23 Drawing Figures

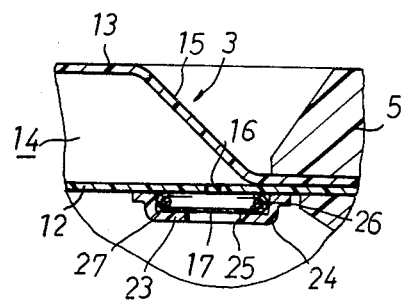
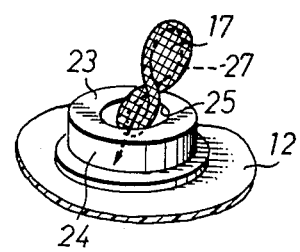
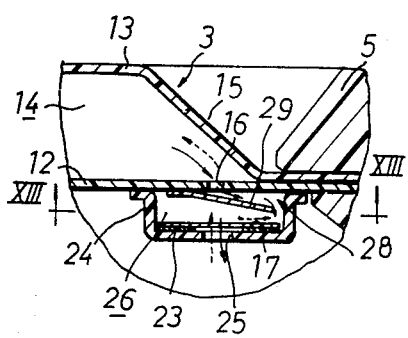
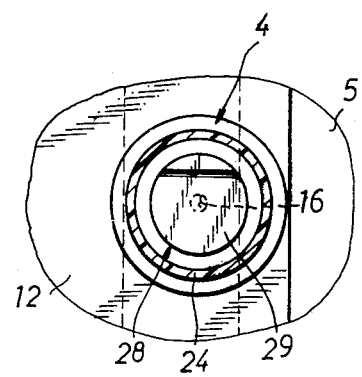
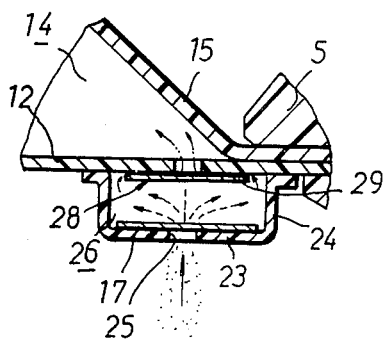
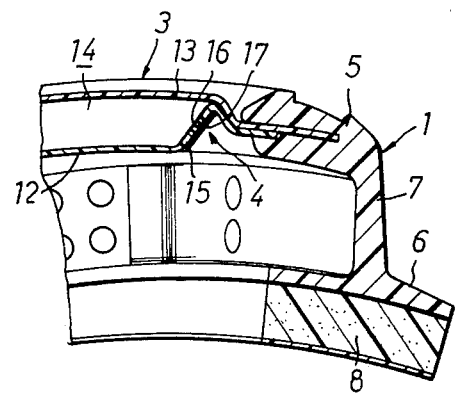

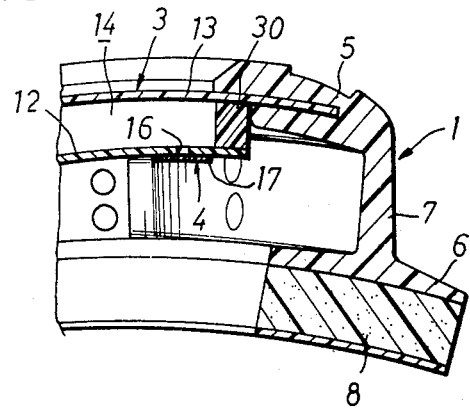
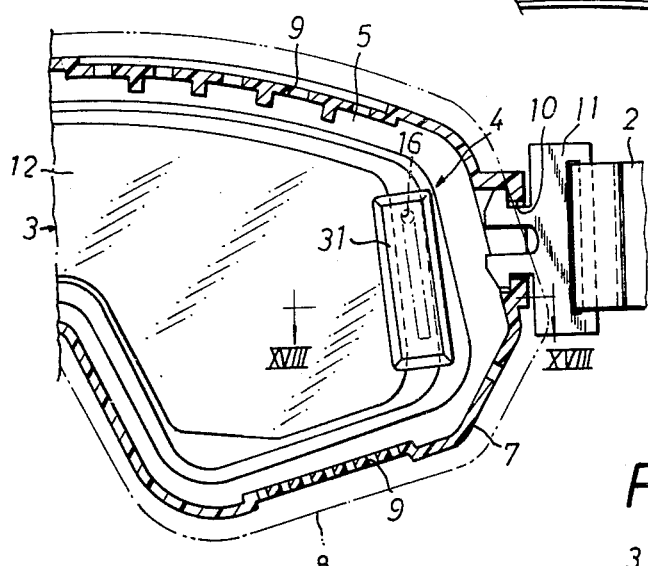
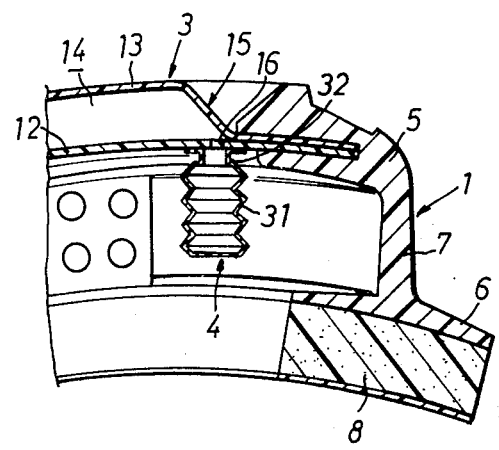
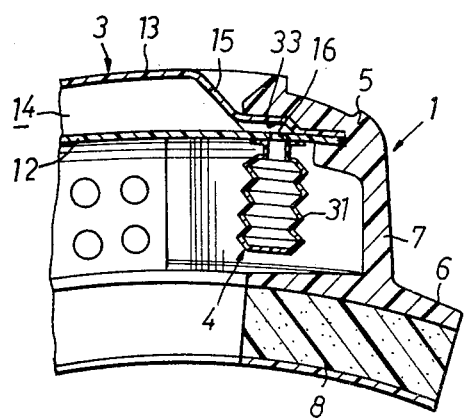

SKI GOGGLES

BACKGROUND OF THE INVENTION

This invention relates to ski goggles, and more particularly to a structure for preventing ski goggle lenses from fogging.

Since the ski goggles are used in a very cold climate as well known, the goggle lens is likely to fog up by virtue of the body temperature or perspiration of the skier during use, especially when the skier comes to a halt, possibly entailing an accident due to an obscured field of view. To prevent the goggle lens from fogging, it has been practice to (1) subject the lens to a chemical antifogging surface treatment, or (2) make the lens from a pair of inner and outer lens plates and form between the lens plates an interior space serving as a heat insulating layer.

These antifogging measures have advantages and disadvantages. The treatment (1) produces an appreciable antifogging effect when the goggle lens has a surface temperature of about 0° C. or higher but is not fully effective in an environment in which the surface temperature drops to 0° C. or a lower level since fog forming droplets of water will freeze on the surface of the goggle lens. In the case of the construction (2) in which the goggle lens comprises two lens plates and has an internal heat insulating space layer, the lens will not be fogged on its front side as by perspiration immediately after the skier comes to a halt but remains free from fog even when the front side lens surface has a temperature of 0° C. or lower.

In order to protect the face for safety during skiing which is a hard exercise, goggle lenses of tough material such as plastics are widely used. Plastics goggle lenses nevertheless have the drawback that the variation in the pressure of the internal space of the lens due to an atmospheric pressure or temperature change during a descent deforms the lens plates and distorts the field of view through the lens. For example, when a goggle lens is used with its interior space sealed off at a great altitude, there arises a pressure difference between the inside and outside of the lens, subjecting the lens to compressive deformation in its entirety and giving a distorted field of view.

Accordingly goggle lenses have already been proposed which include an inner lens plate formed with an air port resembling a pinhole for maintaining the internal pressure of the lens in balance with the outside pressure to prevent the deformation of the lens. The air port formed in the inner lens plate, however, will permit the ingress of water (snow or the like) into the interior space of the lens, with the result that the water, when evaporating with an increase in temperature, fogs up the inside surfaces of the lens plates, rendering the goggle unserviceable as such.

SUMMARY OF THE INVENTION

A first object of the present invention is to provide ski goggles having a goggle lens which comprises a pair of inner and outer lens plates and which has a heat insulating interior space between the lens plates and a pressure balancing air port formed in the inner lens plate close to an outer peripheral portion thereof to prevent the deformation of the lens plates against variations in atmospheric pressure, the goggle lens further being rendered satisfactorily serviceable at all times free from fog by preventing ingress of water into the interior space.

A second object of the invention is to provide ski goggles of the type described in which the air port is adapted to prevent ingress of external air and water therethrough into the interior of the goggle lens when the outside atmospheric pressure rises abruptly owing to a rapid descent or the like, the goggle lens thus being made usable free from fog in an environment involving marked atmospheric pressure variations.

A third object of the invention is to provide ski goggles of the type described in which the interior space of the goggle lens is sealed off from outside to completely prevent ingress of water and thereby ensure a greatly enhanced antifogging effect while effectively preventing the deformation of the lens plates at the same time.

Other objects, features and advantages of the invention will become more apparent from the following description given with reference to the accompanying drawings.

BRIEF DESCRIPTION OF THE DRAWINGS

FIG. 10 is a fragmentary view in section showing a fifth embodiment;

FIG. 11 is a perspective view showing the same while an air filter is being inserted into place;

FIG. 12 is a fragmentary sectional view showing a sixth embodiment;

FIG. 13 is a view in section taken along the line XIII—XIII in FIG. 12;

FIG. 14 is a fragmentary sectional view showing the sixth embodiment and illustrating an inflow of air;

FIG. 15 is a fragmentary sectional view showing a seventh embodiment;

FIG. 16 is a fragmentary sectional view showing an eighth embodiment;

FIG. 17 is a rear view in vertical section showing the right half of a ninth embodiment;

FIG. 18 is an enlarged view in section taken along the line XVIII—XVIII in FIG. 17;

FIG. 19 is a fragmentary sectional view showing a tenth embodiment;

DESCRIPTION OF THE PREFERRED EMBODIMENTS

Figure 1:
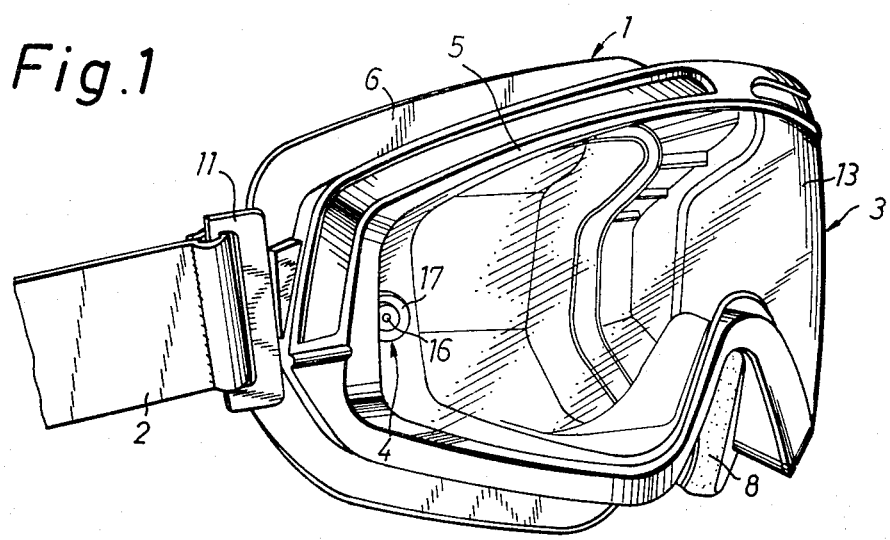
FIG. 1 is an overall perspective view showing a first embodiment of the invention.

FIG. 1 shows the most preferred embodiment of ski goggles of this invention. The ski goggles comprise a goggle frame 1, a rubber band 2 connected to the goggle frame 1, a goggle lens 3 detachably fitted in the frame 1 and means 4 for preventing ingress of water.

Figure 2:
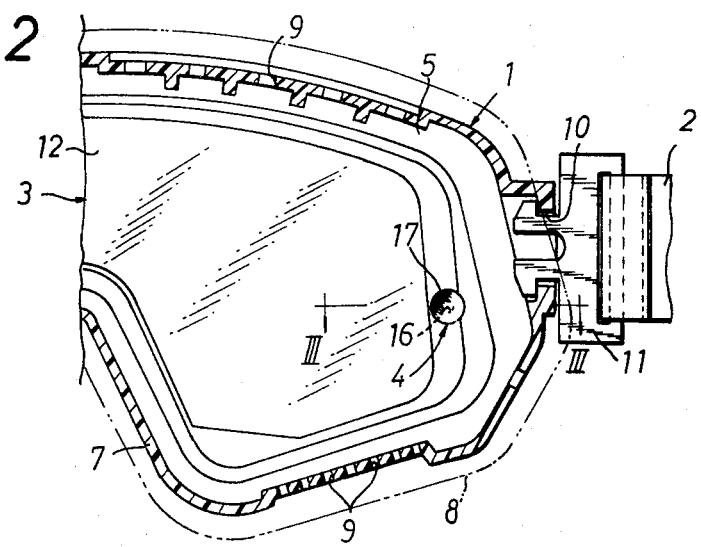
FIG. 2 is a rear view in vertical section showing the right half of the same.
Figure 3:
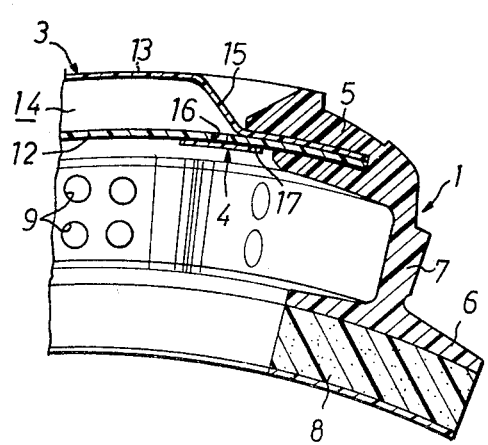
FIG. 3 is an enlarged view in section taken along the line III—III in FIG. 2.

As seen in FIGS. 2 and 3, the goggle frame 1, which is made of a soft material such as vinyl or rubber, includes a lens mounting rim 5, a face fitting member 6 and a peripheral wall 7 interconnecting the rim 5 and the member 6. The lens 3 is detachably mounted on the rim 5. An intimately fittable material 8, such as sponge, is adhered to the face fitting member 6 to ensure intimate contact between the fitting member 6 and the face. The peripheral wall 7 is formed with a desired number of apertures 9 in its upper and lower portions and with cavities 10 at its opposite ends. Connectors 11 at opposite ends of the rubber band 2 are inserted in the cavities 10.

As shown in FIG. 3, the goggle lens 3 comprises a pair of inner and outer lens plates 12 and 13 of colored transparent plastics with a specified interior space 14 formed between the lens plates 12 and 13. The interior space 14 serves as a heat insulating layer. Stated more specifically, the outer lens plate 13 is formed along its outer periphery with a slanting spacer wall 15 integral therewith. The marginal portion of the slanting wall 15 is superposed on and adhered to the outer peripheral portion of the inner lens plate 12, with the result that the slanting wall 15 spaces the outer lens plate 13 from the inner lens plate 12 to provide the interior space 14. Accordingly the interior space 14, serving as a kind of heat insulating layer, reduces the heat transmission between the front and rear sides of the goggle lens 3, such that the temperature of the inner face side of the goggle frame 1 will not be delivered directly to the front side of the outer lens plate 13. Thus the interior space 14 prevents the surface of the outer lens 13 from fogging when the skier comes to a halt during sliding.

The means 4 serves to prevent the entry of water into the interior space 14 of the goggle lens 3 through an air port 16 formed in the inner lens plate 12. As seen in FIGS. 2 and 3, the water ingress preventing means 4 includes a water-repellent air-permeable filter 17 affixed to the inner lens plate 12 in opposed relation to the air port 16. The air port 16 resembles a pinhole and serves to maintain the internal pressure of the space 14 in balance with the external pressure. The air port 16 is formed in one end of the inner lens plate 12 and is positioned as close as possible to the goggle frame 1 in opposed relation to the slanting wall of the outer lens plate 13 so as not to interfere with the field of view. Thus the provision of the preventing means 4 produces little or no influence on the overall field of view through the goggle lens 3, consequently assuring the largest possible field of view needed for skiing.

Figure 4:
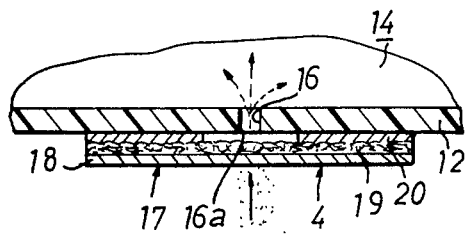
FIG. 4 is an enlarged fragmentary view of FIG. 3.
Figure 5:
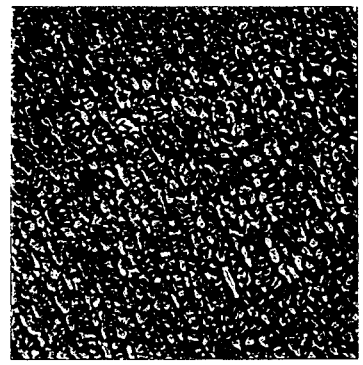
FIG. 5 is a diagram showing a layer of ethylene tetrafluoride resin fibers.

With reference to FIG. 4, the water-repellent air-permeable filter 17 comprises an air-permeable backing sheet 18, such as nylon fabric, and a layer of porous material 19, such as a layer of ethylene tetrafluoride resin fibers, having continuous pores and affixed to the backing sheet 18. As illustrated on an enlarged scale in FIG. 5, the layer of ethylene tetrafluoride resin fibers, 19, is composed of very tough, flexible, fine, drawn fibers, has high water repellency and includes numerous pores extending therethrough. The resin fiber layer 19 has the following characteristics:

Average pore size ($\mu$): 0.2–5.0
Porosity (%): 25–95
Air flow rate (cc/min/in$^2$): 0.1–3,000 (4.88 in. H$_2$O)

With a rise in the external atmospheric pressure, for example, due to a descent, external air flows through the air port 16 into the interior space 14 of the lens 3 as indicated by arrows in FIG. 4, bringing the internal pressure of the space 14 into balance with the external pressure and enabling the lens plates 12 and 13 to remain free of any deformation and afford a proper field of view without distortion. The flow of air into the interior space 14 via the air port 16 takes place through the resin fiber layer 19 of the filter 17, so that even when the external air contains a large amount of water or when there is snow or like deposit on the outer surface of the air-permeable backing sheet 18, the ingress of water into the interior space 14 can be prevented by the water repellency of the air-permeable filter 17. Despite the provision of the air port 16, the inner surfaces of the lens 3 defining the interior space 14 can therefore be prevented from fogging to assure a satisfactory view at all times.

As shown in FIG. 4, the filter 17 is affixed to the inner lens plate 12 with the ethylene tetrafluoride resin fiber layer 19 facing the lens plate, using an adhesive 20. Since the filter 17 itself is in the form of a very thin sheet and the fiber layer 19 is covered with the air-permeable backing sheet 18 for protection, the filter 17 will cause no trouble when wiping the goggle lens 3, especially the inner lens plate 12, for the removal of snow, stain or the like, thus permitting easy cleaning without any possibility of causing damage to the fiber layer 19 by wiping. The filter is therefore durable and retains the desired water repellency, namely, the desired antifogging effect over a prolonged period of time. The adhesive 20 is applied to the peripheral portion of the filter 17 to avoid clogging of the air port 16. The filter 17, which is affixed to the inner lens plate 12 with the adhesive 20, can be forcibly peeled off the plate for replacement with a new one when clogged. When affixing the filter 17, the adhesive 20 may be applied in the form of a layer of relatively large thickness as seen in FIG. 4 to space the filter 17 from the inner lens plate 12 by a small distance. The filter 17 then will not be cut by the port defining edge 16a even when depressed for cleaning.

Figure 6:
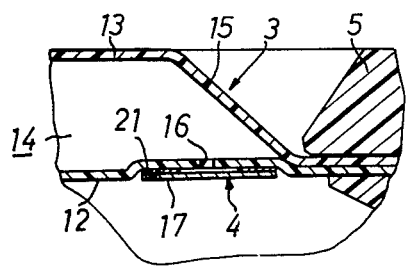
FIG. 6 is a fragmentary sectional view showing a second embodiment.

FIG. 6 shows another embodiment in which the water ingress preventing means 4 in FIG. 3 is disposed in a circular recessed portion 21 formed in the inner lens plate 12 and projecting into the interior space 14. The recessed portion 21 is formed with an air port 16 and has accommodated therein an air-permeable filter 17, which can be very effectively prevented from being peeled off as by cleaning. With use of an adhesive or tackified composition, the filter 17 could be displaced relative to the air port 16 if inadvertently subjected to a force acting in the direction of its plane as when the goggle lens 3 is to be fitted into the frame 1, but this problem is also avoidable when the filter 17 is accommodated in the recessed portion 21.

FIGS. 7 to 11 show other embodiments in which the filter 17 is similarly protected.

Figure 7:
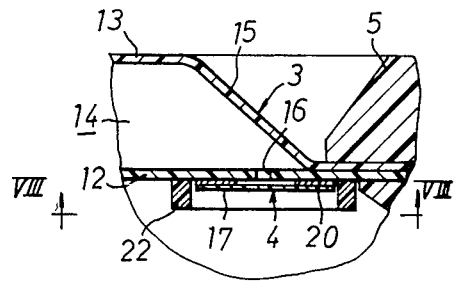
FIG. 7 is a fragmentary sectional view showing a third embodiment.
Figure 8:
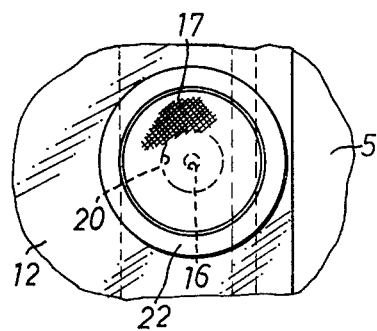
FIG. 8 is a view showing the same as it is seen in the direction of the arrows VIII—VIII in FIG. 7.

FIGS. 7 and 8 show an annular filter frame 22 slightly diametrically larger than the filter 17. The filter frame 22 is adhered to the inner lens plate 12, as arranged substantially concentrically with the filter 17. The frame 22 has such a diameter and height that the finger of the user will not contact the filter directly.

Figure 9:
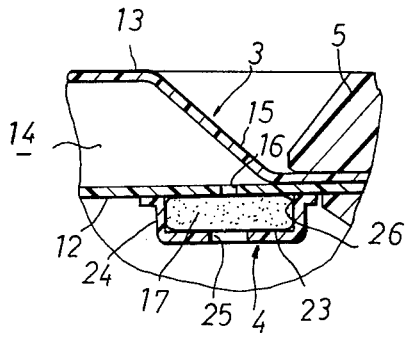
FIG. 9 is a fragmentary sectional view showing a fourth embodiment.

The embodiment shown in FIG. 9 includes a filter frame 24 having a bottom 23 formed with an opening 25 diametrically larger than the air port 16. The frame 24 has an interior space 26 for accommodating a filter. The filter 17 can be installed in position merely when placed into the space 26. Thus there is no need to use an adhesive or the like. If the opening 25 has a large diameter and sponge, nonwoven fabric or the like rendered water-repellent is used as the air-permeable filter 17, the filter 17 is replaceable through the opening 25 when stained or clogged after a long period of use.

When the filter 17 is in the form of a sheet, the filter may be used as attached to an elastic ring 27 of plastics, rubber or the like as shown in FIG. 10. The filter 17 can then be easily placed into the space 26 through the opening 25 if the elastic ring 27 is twisted as shown in FIG. 11. Upon placement into the space 26, the ring 27 restores itself, stretching the filter within the space 26 for proper installation as illustrated in FIG. 10. In either of the embodiments of FIGS. 9 and 10, the filter 17 is withdrawable by engaging the filter with a pin or the like and drawing out the filter from the opening 25.

FIGS. 12 and 13 show another embodiment in which the air-permeable filter 17 is in combination with a regulating valve 28. The filter 17 is affixed to the inner side of the bottom 23 of a filter frame 24 and opposed to an opening 25. The regulating valve 28 reduces the flow of air through the air port 16 when the external pressure greatly rises. The valve comprises a circular valve disk 29 blanked out from a vinyl sheet, rubber sheet or the like, disposed within the interior space 26 of the filter frame 24 and attached at a peripheral portion thereof to the inner lens plate 12. The free end of the valve disk 29 is movable to open or close the air port 16.

The disk 29 of the regulating valve 28 usually leaves the air port 16 open as shown in FIG. 12, permitting the interior space 14 of the goggle lens 3 to communicate with the outside at the same pressure via the air port 16, filter accommodating space 26 and opening 25, while water only is prevented from entering the interior space 14 by the filter 17. When the external pressure tends to rise moderately as when the skier starts to glide down a gentle slope, the valve disk 29 remains in an opened position similar to the position shown in FIG. 12, holding the internal pressure of the space 14 in balance with the outside pressure by way of the air port 16.

When the skier glides down a steep slope with a rapid rise of the atmospheric pressure, the increased pressure presses the valve disk 29 against the inner lens plate 12 as seen in FIG. 14, with the result that external air flows through a small clearance between the valve disk 29 and the inner lens plate 12 and enters the interior space 14 through the air port 16. Thus the valve is closed to a greater extent. In the absence of the valve 28, the abrupt rise of the atmospheric pressure would cause air to flow through the filter 17 at a rate corresponding to the pressure difference involved, with the result that the water, such as snow or water droplets, on the filter 17 would be forced into the interior space 14 along with the air. The regulating valve 28 nevertheless permits the air through the filter 17 to flow into the interior space 14 at a greatly reduced rate, while enabling the filter 17 to retain its water repellency to prevent the ingress of the water and produce a sufficient antifogging effect on the goggle lens 3. Although a pressure difference occurs between the inside and outside of the goggle lens 3 at this time, the inner and outer lens plates 12 and 13 will deform only to a slight extent that is not substantially objectionable to skiing without undergoing marked deformation, because the interior space 14 is not closed completely but is held in communication with the outside through the greatly closed valve 28 to permit slow ingress of external air. Accordingly the provision of the regulating valve 28 renders the goggles well-suited for use on steep slopes.

The goggle lens 3 is not limited to the construction in which the outer lens plate 13 has a slanting wall 15. As shown in FIG. 15, for example, the slanting wall 15 may be formed on the inner lens plate 12 to join the lens plates 12 and 13 at the outer peripheral portion of the slanting wall 15. Alternatively the inner and outer lens plates 12 and 13 may be connected together by a spacer frame 30. The embodiment of FIG. 15 is provided with water ingress preventing means 4 on the slanting wall 15 of the inner lens plate 12. With the embodiment of FIG. 16, the water ingress preventing means 4 can be attached to the spacer frame 30.

Instead of providing the filter 17 on the outer side of the inner lens plate 12, it is also possible to dispose the filter on the inner side of the inner lens plate 12, namely, inside the interior space 14. Furthermore, instead of using the layer of ethylene tetrafluoride resin fibers, 19, for the filter 17, a layer of silicone resin fibers is usable.

While the water ingress preventing means 4 described above comprise an air port 16 and an air-permeable filter 17 in combination, the interior space 14 can be sealed off and completely separated from the outside with use of an inflatable balancing container as shown in FIG. 17 et seq.

The embodiment shown in FIGS. 17 and 18 includes a plastics bellows container 31 capable of retaining its shape and serving as the balancing container. The container 31 has an upper end mouth 32 adhered to the inner lens plate 12 in communication with an air port 16. The interior space 14 of this embodiment is in communication the bellows container 31 alone by way of the air port 16 but is completely separated from the outside, so that no water enters the interior space 14 from outside. This affords a greatly enhanced antifogging effect. When a variation occurs in the outside atmospheric pressure, the bellows container 31 will inflate or contract accordingly, thereby bringing the internal pressure of the interior space into balance with the atmospheric pressure. When the atmospheric pressure increases, for example, the bellows container 31 is compressed, causing the inside air to flow through the air port 16 into the interior space 14 to pressurize the space 14 and bring the internal pressure of the lens 3 into balance with the outside pressure, whereby the deformation of the inner and outer lens plates 12 and 13 can be avoided. If the bellows container 31 has a vertically elongated shape and disposed along the goggle frame 1 as seen in FIG. 17, the influence of the container on the field of view can be minimized. The air port 16 may be in the form of a slot as indicated in a two-dot-and-dash line in FIG. 17.

Figure 20:
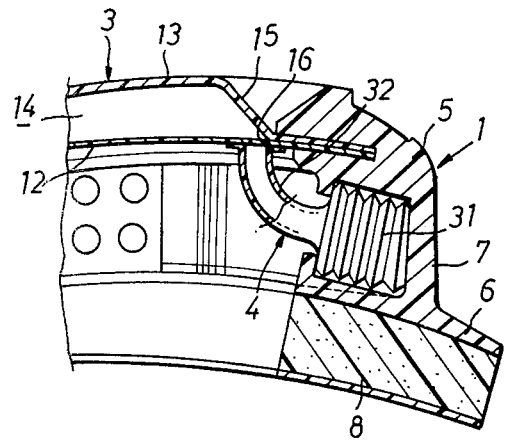
FIG. 20 is a fragmentary sectional view showing an eleventh embodiment.

To assure the desired field of view in this case, the slanting wall 15 on the outer lens plate 13 may be made to extend outward to provide a channel 33, with the air port 16 and the bellows container 31 opposed to the outer end of the channel 33 as shown in FIG. 19, or an elongated mouth portion 32 may be provided as seen in FIG. 20, whereby the bellows container 31 can be accommodated within the goggle frame 1. FIG. 20 shows a projection 34 for holding the bellows container 31 in place.

Figure 21:
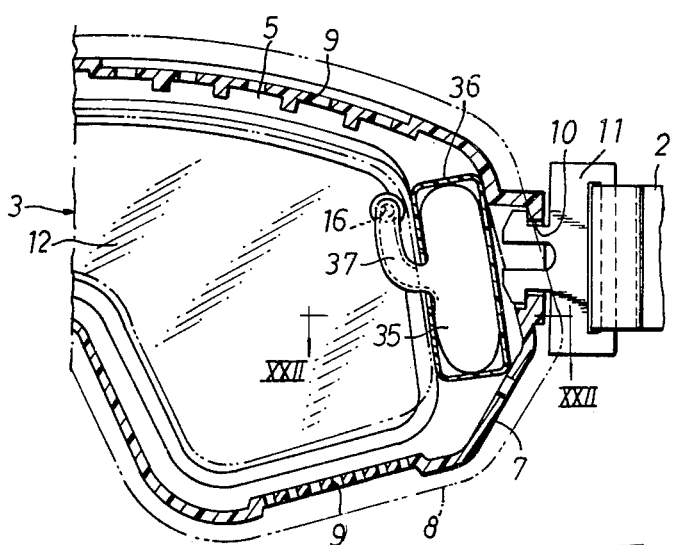
FIG. 21 is a rear view in vertical section showing the right half of a twelfth embodiment.
Figure 22:
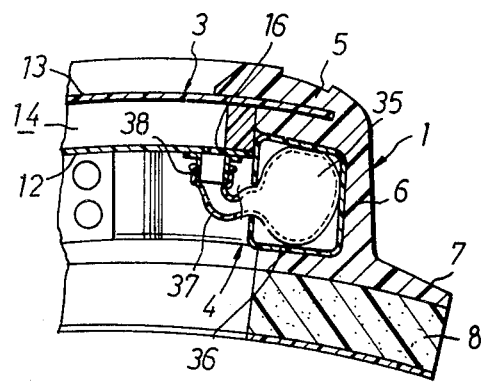
FIG. 22 is an enlarged view in section taken along the line XXII—XXII in FIG. 21.

The embodiment shown in FIGS. 21 and 22 includes an elastic container 35, such as a rubber balloon, serving as the balancing container. The elastic container 35 is housed in a vertically elongated protective case 36 and has a mouth 37 connected to a tubular connector 38. The connector 38 is adhered to the inner lens plate 12 and opposed to the air port 16. The protective case 38 is detachably fitted in the goggle frame 1 at its one end.

The elastic container 35 functions in the same manner as above to bring the internal pressure of the lens 3 into balance with the outside pressure and prevent the deformation thereof. Since the elastic container 35 is deformable in conformity with the shape of the protective case 36, it is very convenient for use in a limited space.

Figure 23:
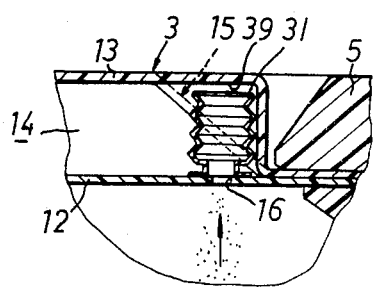
FIG. 23 is a fragmentary sectional view showing a thirteenth embodiment.

The balancing container, such as the bellows container 31, needs only to have such a capacity as to accommodate the pressure difference between the outside and inside the goggle lens 3, hence of relatively small capacity. Accordingly the slanting wall 15 of the outer lens plate 13 can be formed with an accommodating portion 39 for disposing the bellows container 31 inside the inner lens plate 12, namely, within the interior space 14 of the lens 3 as shown in FIG. 23. The bellows container 31, which is then in communication with the outside via the air port 16, produces the same antifogging and deformation preventing effects as already described.

Bags having no shape retentivity or no elasticity are also fully useful as balancing containers.

What is claimed is:

1. Ski goggles including a goggle lens comprising a pair of inner and outer lens plates and having a heat insulating interior space between the lens plates, the inner lens plate being formed with a pressure balancing air port close to an outer peripheral portion thereof, the ski goggles being characterized in that means is provided in opposed relation to the air port for preventing ingress of water into the interior space while permitting flow of air therethrough, the water ingress preventing means including a water-repellent air-permeable filter.

2. Ski goggles as defined in claim 1 wherein at least one of the inner and outer lens plates is formed with a slanting spacer wall along its outer periphery, and the air port and the water-repellent air-permeable filter are disposed in opposed relation to the slanting wall.

3. Ski goggles as defined in claim 1 or 2 wherein the water-repellent air-permeable filter comprises an air-permeable backing sheet and a porous layer having continuous pores, made of ethylene tetrafluoride resin fibers and affixed to the sheet.

4. Ski goggles including a goggle lens comprising a pair of inner and outer lens plates and having a heat insulating interior space between the lens plates, the inner lens plate being formed with a pressure balancing air port close to an outer peripheral portion thereof, the ski goggles being characterized in that means is provided in opposed relation to the air port for preventing ingress of water into the interior space while permitting flow of air therethrough, the water ingress preventing means including a filter frame surrounding the air port and attached to the inner lens plate, the filter frame having accommodated therein a water-repellent air-permeable filter and a regulating valve closable to a reduced opening when the external pressure rises rapidly.

5. Ski goggles as defined in claim 4 wherein at least one of the inner and outer lens plates is formed with a slanting spacer wall along its outer periphery, and the air port, the filter frame, the water-repellent air-permeable filter and the regulating valve are disposed in opposed relation to the slanting wall.

6. Ski goggles as defined in claim 4 or 5 wherein the water-repellent air-permeable filter comprises an air-permeable backing sheet and a porous layer affixed to the sheet, having continuous pores and made of ethylene tetrafluoride resin fibers.

* * * * *